US006486212B2

(12) United States Patent
Meinert

(10) Patent No.: US 6,486,212 B2
(45) Date of Patent: Nov. 26, 2002

(54) SEMIFLUORINATED ALKANES AND THE USE THEREOF

(76) Inventor: Hasso Meinert, Hafnerweg 7, D-89231 Ulm (DE)

( * ) Notice: Subject to any disclaimer, the term of this patent is extended or adjusted under 35 U.S.C. 154(b) by 0 days.

(21) Appl. No.: 09/854,634

(22) Filed: May 15, 2001

(65) Prior Publication Data

US 2002/0128527 A1 Sep. 12, 2002

Related U.S. Application Data

(62) Division of application No. 09/043,489, filed as application No. PCT/EP96/03542 on Aug. 9, 1996, now Pat. No. 6,262,126.

(30) Foreign Application Priority Data

Sep. 29, 1995 (DE) .......................... 195 36 504

(51) Int. Cl.[7] .............................................. A61K 47/00
(52) U.S. Cl. ...................................... 514/759; 570/134
(58) Field of Search ........................... 514/759; 570/134

(56) References Cited

U.S. PATENT DOCUMENTS

| 2,997,505 A | | 8/1961 | McBee et al. | |
|---|---|---|---|---|
| 3,979,469 A | * | 9/1976 | Jager | 260/653 |
| 5,202,041 A | * | 4/1993 | Traverso | 252/58 |
| 5,423,994 A | * | 6/1995 | Traverso et al. | 252/58 |
| 5,441,733 A | * | 8/1995 | Meinert | 424/78.04 |
| 6,113,919 A | * | 9/2000 | Reiss et al. | |

FOREIGN PATENT DOCUMENTS

| DE | 39 25 525 A1 | | 2/1991 |
|---|---|---|---|
| EP | 0 444 752 A1 | | 9/1991 |
| EP | 0 563 446 A1 | | 10/1993 |
| GB | 1364495 | * | 8/1974 |
| WO | 93/01798 | * | 2/1993 |

OTHER PUBLICATIONS

Twieg et al., "Synthesis and characterization of perfluoro-alkylalkanes (PFAA) as models for semiflexible polymers," Chemical Abstracts, vol. 101, No. 2, Jul. 9, 1984.

* cited by examiner

Primary Examiner—Alan Siegel
(74) Attorney, Agent, or Firm—Crowell & Moring LLP

(57) ABSTRACT

The invention concerns semi-fluorinated alkanes of the general formulae $R_F R_H$ or $R_F R_H R_F$, $R_F$ being a linear or branched perfluoroalkyl group and $R_H$ being a linear or branched saturated (hydrocarbon)-alkyl group.

3 Claims, 3 Drawing Sheets

SEMIFLUORINATED ALKANES AND THE USE THEREOF

This application is a division of application Ser. No. 09/043,489, filed Sep. 3, 1998 now U.S. Pat. No. 6,262,126 which is a 371 of PCT/EP96/03542 filed Aug. 9, 1996.

BACKGROUND AND SUMMARY OF THE INVENTION

This invention relates to semifluorinated alkanes of the general formulas

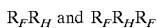
$R_F R_H$ and $R_F R_H R_F$ wherein $R_F$ is a linear or branched perfluoralkyl group and $R_H$ is a linear or branched, saturated (hydrocarbon)-alkyl group.

The unbranched semifluorinated alkanes have the formulas:

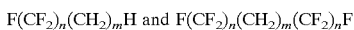
$F(CF_2)_n(CH_2)_mH$ and $F(CF_2)_n(CH_2)_m(CF_2)_nF$ wherein n=1–20 and m=3–20.

The branched semifluorinated alkanes can also contain within the perfluoralkyl groups FCX units wherein $X=C_2F_5$, $C_3F_7$ or $C_4F_9$ as well as —HCY— units within the alkyl groups wherein $Y=C_2H_5$, $C_3H_7$ or $C_4H_9$.

A —$CX_2$— group can be contained within a perfluoralkyl chain, and a —$CY_2$— group within an alkyl chain.

Instead of the perfluoralkyl group $F_3C$—, an $FCX_2$— or $F_2CX$— group, with $X=C_2F_5$, $C_3F_7$ or $C_4F_9$, can be bound in the terminal position in the molecule, and likewise an $HCY_2$— or $H_2CY$— group wherein $Y=C_2H_5$, $C_3H_7$, or $C_4H_9$ can be found in the terminal position in the molecule instead of the alkyl group $H_3C$—.

But in the case of all of the named isomers, that is to say linear or branched semifluorinated alkanes, the total number of the carbon atoms in the perfluoralkyl part remains, as stated, within the limits of n=1–20, and also in the alkyl part the number of the carbon atoms remains in the stated limits of m=3–20.

The invention furthermore relates to the use of these semifluorinated alkanes in medicine, pharmacy, biology and technology.

These semifluorinated alkanes, also called diblock compounds $R_F R_H$ and triblock compounds $R_F R_H R_F$, or also "modified perfluorocarbons," can be linear or branched both in the perfluoralkyl groups and in the alkyl groups, while in the case of the isomers the total number of the carbon atoms in the perfluoralkyl part remains in the stated limits of n=1 to 20 and in the alkyl part the total number of carbon atoms remains in the stated limits of m=3 to 20.

These semifluorinated alkanes can be used as medicinal adjuvants, drugs for ophthalmology, as a vitreous humor substitute, as a dermal treatment for supporting oxygen transport in the skin, for instillation and fluid artificial respiration in surgical interventions and in emergency medical treatment, to facilitate breathing in divers, and as friction-reducing additives in lubricants and waxes.

These types of compounds proposed as patent-worthy are similar to the perfluorocarbons (compounds which consist only of carbon-fluorine bonds) are chemically, physically and physiologically inert and thus nontoxic.

In comparison with the perfluorocarbons, the semifluorinated diblock or triblock alkanes are of an entirely different structure. They consist of closed hydrocarbon-alkane groups, —$(CH_2)_n$— and —$(CHR_H)_n$— and —$(CH_2)_nH$, which are bound directly to perfluoralkyl groups, —$(CF_2)_m$— and —$(CFR_F)$— and —$(CF_2)F$, respectively. The perfluoralkyl part can also begin with a $(CR_FR_FF)$— grouping and terminate in a $(CR_HR_HH)$ grouping. Within a perfluoralkyl chain an —$R_FCR_F$— group can be bound, and within an alkyl chain an —$R_HCR_H$— group can be bound.

In these types of compounds no intramolecular HF cleavage with the formation of fluorolefinic double bonds can take place. On the contrary, the closed hydrocarbon-alkane grouping has a bond strengthening effect on the sometimes very strong C—F bonds in the perfluoralkyl part of the compound in question.

The semifluorinated diblock or triblock alkanes are colorless liquids or solids. They are not attacked by strong acids or lyes or oxidants or nucleophiles, much less liable to metabolic or catabolic attack.

Physically, the semifluorinated alkanes behave like modified perfluorocarbons, and the boiling points and melting points increase with increasing molecular mass (see FIGS. 1 and 2). Semifluorinated alkanes, like the pure perfluorocarbons, have a high solubility for gases, including $O_2$ and $CO_2$ (about 40–50 and 130–150 vol. %, respectively).

Like the perfluorocarbons and the hydrocarbons, the semifluorinated alkanes are scarcely or not at all soluble.

However, they can be converted in a manner similar to H. Meinert, A. Knoblich, Biomat. Art. Cells & Immob. Biotech., 21 (1993) 583 by means of effective tensides (fluorotensides, compounds with a fluorophilic head and a hydrophilic tail, ethylene oxide-propylene oxide block polymers, Pluronics® or phospholipids such as egg lecithin or soya lecithin, etc.) or ionic tensides, with the aid of physical emulsification methods (ultrasound or Gaulin homogenizers), to particle-stable emulsions with particle sizes of about 100–300 nm.

In contradistinction to the perfluorocarbons, the semifluorinated alkanes, regardless of their $R_F$ or $R_H$ content, are soluble both in perfluorocarbons and derivatives of perfluorocarbons (perfluorinated ethers of higher molecular weight, Hostinert®, Fomblin®, etc.) [see H. Meinert, A. Knoblich, Biomat. Art. Cells & Immob. Biotech., 21 (1993) 583; H. Meinert, Fluorine in Medicine in the 21st Century, Manchester (1994), paper 23; R. J. Twieg et al., Macromolecules 18 (1985) 1361; and J. Höpken et al., Macromol. Chem. 189 (1988) 911] and in hydrocarbons and their derivatives and compounds with higher alkyl group contents (e.g., liquid paraffins, silicone oils, fatty acid esters, etc.). As the perfluoralkyl content increases the solubility in the fluorocarbon systems increases, while with increasing alkyl content the solubility in hydrocarbon systems increases, and vice-versa. In solutions of semifluorinated alkanes, especially semifluorinated linear alkanes, in hydrocarbon substances, laminar double layers may be present, while under certain circumstances, e.g. depending on the concentration ratio or upon cooling, the previously homogeneous, optically clear solutions turn into opaque gels. Upon subsequent cooling the homogeneous solutions are recovered. The formation of the gel is due to the fact that the solvent hydrocarbons are absorbed by the diblock double layers of the $R_F R_H$ [R. J. Twieg et al., Macromolecules 18 (1985) 1361; J. Höpken et al., Macromol. Chem. 189 (1988) 911].

In contrast to the perfluorocarbons (densities 1.8–2.0 g/cm³) the densities of the semifluorinated alkanes with densities between 1.1 and 1.7 g/cm³ are substantially lower due to the fact that these molecules have a high content of hydrocarbon groupings.

On the other hand, the proposed compounds have the preferred properties of the perfluorocarbons in regard to their boundary surface tension against water ($R_F R_H$ 50–58 nN/m at 20° C.) and the extraordinarily low surface tension ($R_F R_H$ 25–22 mN/m at 20° C., due to the fact that perfluoralkyl groups are bonded to the end of the molecule.

If separation occurs in long-standing solutions of the above-mentioned hydrocarbons and their derivatives with semifluorinated diblock or triblock alkanes due to relatively great differences in density (which occurs when semifluorinated alkanes with a high perfluoralkyl content are used), the homogeneous, optically clear solution can be restored by simple shaking.

The semifluorinated diblock or triblock alkanes are obtained by the reaction of perfluoralkyl iodides with alkenes or α,ω-dienes, after HI elimination followed by hydrogenation by means of a platinum catalyst Organikum, Autorenkollektiv, Dtsch. Verlag der Wissenschaften, Berlin (1977) 363 or by means of tributyltin hydride [J. Höpken et al., Macromol. Chem. 189 (1988) 911] (see the Examples of syntheses of semifluorinated diblock and triblock alkanes below).

The products thereby obtained for the proposed fields of application can, in a preferred embodiment, also be highly purified. For that purpose the semifluorinated alkanes are first treated with acid permanganate solution in a manner similar to DE 42 05 341 (WO 93/16974), then they are refluxed or autoclaved for about 72 hours at 150–180° C. with a mixture of strong aqueous caustic soda solution (4–8 n), CaO or BaO, and a nucleophilic agent (e.g., secondary amine). The reaction product is finally obtained by means of a separatory funnel from the aqueous alkaline phase, which in a given case still contains alcohol, and the amine phase is separated, treated repeatedly in succession with dilute mineral acid, $NaHCO_3$ solution, distilled water, anhydrous $Na_2SO_4$ and anhydrous $CaCl_2$ and fractionally distilled through an efficient column.

The semifluorinated alkanes thus treated are found by infrared, IH-NMR, $^{19}$F-NMR, and GC-/MS spectroscopy to be free of groupings which might lead by intramolecular HF elimination to the formation of toxic olefinic byproducts.

A suitable quantitative method for the determination of groupings that can lead to the intramolecular cleavage of HF or to the exchange of a fluorine atom bound to the carbon by means of a nucleophilic agent is, according to DE 42 05 341 (WO 93/16974), the determination of ionizable fluoride in the reaction of the sample material with hexamethylenediamine in nonane or decane by several hours of heating at 120–150° C., and detecting any freed fluoride by means of an ion-sensitive electrode. After the purification process, accordingly, no more fluoride ions were detectable (detection limit for the fluoride concentration $\leq 10^{-5}$ mol/l$^-$1).

The highly purified semifluorinated alkanes show no inhibition of proliferation in regard to DNS and protein synthesis on HeLa or Molt4 or $HEP_2$ cell cultures. Thus the semifluorinated alkanes named in accord with the invention are directly usable for medical, pharmaceutical and biological purposes.

The semifluorinated alkanes according to the invention can find many different uses, namely the use of linear or branched semifluorinated alkanes as medical adjuvants, as drugs for ophthalmology, as vitreous humor substitute, as a dermal treatment agent, for fluid artificial respiration by intubation, and as a friction-reducing additive for lubricant oils and waxes.

It is known that liquid perfluorocarbons, on account of their high density and low surface tension and boundary surface tension are suitable as a fluid for the reattachment (unfolding) of a detached retina to the choroid of the eye U.S. Pat. No. 4,490,351 (EP 0 112 658) U.S. Pat. No. 5,397,805 (EP 0 493 677, DE 41 00 059. Certainly perfluorocarbons are not appropriate for permanent tamponing on account of their high density and the resultant high pressure on the choroid.

It is furthermore known that, by the use of modified perfluorocarbons the disadvantageous effect of the excessive density in comparison with pure perfluorocarbons can be obviated DE 42 11 958 (EP 0 563 446), although in this case only diblock and triblock compounds with $R_F=CF_3$ and $C_2F_5$, and $R_H=CH_3(CH_2)_n$ where n=2–10 are used.

The diblock and triblock compounds of the semifluorinated alkanes listed in claim 1 have broader applications, especially those of the types $F(CF_2)_n(CH_2)_mH$ and $F(CF_2)_n(CH_2)_m(CF_2)_nF$ where n=3–20 and m=3–20 as well as their branched isomers, because with the lengthening of both the $R_F$ and $R_H$ content in the molecule, the solubilities in perfluorocarbon and in hydrocarbon systems are significantly broadened. The liquid representatives of the semifluorinated alkanes (see FIGS. 1 and 2) can be used on account of their outstanding physical properties directly for the unfolding of the retina; they are suitable as very stable colorless fluids for laser coagulation, because no degradation products are formed by the laser beam.

The semifluorinated alkanes according to the invention are suitable for retinal reattachment, the same as the pure perfluorocarbons U.S. Pat. No. 4,490,351 (EP 0 112 658) U.S. Pat. No. 5,397,805 (EP 0 493 677, DE 41 00 059 and the modified perfluorocarbons claimed in DE 42 11 958 (EP 0 563 446). Furthermore, the linear or branched semifluorinated alkanes are especially appropriate for ophthalmic treatment, especially when they have a relatively high alkyl content, —$(CH_2)_n$—, —$(CH_2)_nH$ and their $R_H$-substituted isomers, due to their ability to dissolve medication as well as their ability to be dyed.

The proposed semifluorinated diblock and triblock alkanes with a high $R_F$ content are easily soluble in the perfluorocarbons long used for retinal reattachment [S. Chang et al., Am. J. Ophthalmol. 103 (1987) 29; S. Chang et al., Am. J. Ophthalmol. 103 (1987) 38; S. Chang et al., Ophthalmology 96 (1989) 785; G. A. Peyman et al., Internal Tamponade in Vitreoretinal Surgery, Ravenna (1994), paper 33], so that in retinal reattachment variations are possible in regard to the densities and boundary surface characteristics, if homogeneous mixtures of semifluorinated alkanes with perfluorocarbons are applied.

Moreover, the semifluorinated alkanes according to the invention, especially the diblock compounds of the $R_F R_H$ type with a high $R_H$ content are suitable as solvents for the medications to be used in ophthalmology.

Thus, for example, medicaments such as 5-fluoruracil, Retinol® or Daucomycin among others are moderately to easily soluble.

In the case of retinol the solution is colored and therefore easily visible. This is advantageous to surgeons in dealing with the reattachment fluid in retinal reattachment.

It is known to use as a postoperative tamponade a combination of perfluorophenanthrene, Vitreon® and silicone oil [G. A. Peyman et al., Internal Tamponade in Vitreoretinal Surgery, Ravenna (1994), paper 33]. Because, however, on account of the insolubility of the perfluorocarbon in the silicone oil, such a combination of two non-miscible fluids consists of different densities, the result in the real system of a moving eye will be difficulties in regard to transparency and "emulsification" at the boundary surface of the two tamponade fluids.

On the other hand, the semifluorinated alkanes of the invention, especially the linear representatives of the $R_FR_H$, have good solubility in silicone oils. The semifluorinated alkanes are more soluble in silicone oils the higher the $R_H$ content is. For example, in the silicone oils most used for the silicone oil tamponade and having 5000 mPa/s or 1000 mPa/s, the fluid semifluorinated diblock compounds $C_6F_{13}C_8H_{17}$ or $C_4F_9C_5H_{11}$ or $C_2F_5C_8H17$ are uniformly soluble. For example, these $R_FR_H$'s dissolve in silicone oil of 1000 mPa/s in ratios of 2:1 to 1:2. The solubilities decrease as the viscosity of the silicone oil increases.

Thus there is a completely new application for such homogeneous solutions of $R_FR_H$'s in silicone oils, on account of the resultant adjustable low densities (1.0–1.3) and the selectable boundary surface and surface tensions (see Table 1), for the long-term tamponade.

TABLE 1

|  | Boundary surface tension against water in mN/m (24° C.) | Surface tension in mN/m (24° C.) |
| --- | --- | --- |
| Silicone oil 1000 mPas | 23.3 | 22.2 |
| $C_6F_{13}$—$C_8H_{17}$ | 49.0 | 21.1 |
| 1:1 mixture (silicone oil 1000/$C_6F_{13}$—$C_8H_{17}$) | 26.6 | 20.9 |

Since the semifluorinated alkanes are solvents for perfluorocarbons it is also possible to transform solutions of perfluorocarbons to semifluorinated alkanes, especially of the $R_FR_H$ type, with the corresponding silicone oils, to homogeneous, optically clear systems and then use them for the tamponade.

Moreover, with these semifluorinated alkanes, especially the linear $R_FR_H$'s with a relatively high $R_H$ content, an outstanding diluent and wash fluid for silicone oils after a silicone oil retinal tamponade. Heretofore, the only way to remove silicone oils thoroughly from the eye has been to extract them with a cannula and syringe.

It is known to affect the oxygen status of the skin by making oxygen available for metabolic processes in the skin by means of biologically inert, oxygen-dissolving perfluorocarbons, in addition to and independently of the vascular system of the living organism. In U.S. Pat. No. 4,366,169 the use of perfluorocarbons is claimed for the treatment of skin injuries and wounds, especially burns, wherein the oxygen-containing perfluorocarbon is placed either directly or in the form of an emulsion on the skin, on bandages, or other such means.

In J. Höpken et al., Macromol. Chem. 189 (1988) 911 the preparation is described of gel with gas transporting properties for application to the skin, wherein, for example, a perfluorocarbon is first converted to a gel by means of a tenside and an emulsification, and finally a difficult separation is made between the gel phase and the aqueous phase. This gel is applied to the skin in appropriate formulations, and it operates there, but without penetrating the stratum corneum.

In EP 29 66 61 a single-phase system containing perfluorocarbon is described, which can act in the cosmetic field and as a lotion to promote oxygen transportation. Perfluorocarbons with a maximum concentration of 50% are emulsified in water with perfluorinated emulsifiers of the alkanesulfonic acid amide type in the presence of an aliphatic alcohol as an emulsifying aid.

In DE 41 27 442 and DE 42 21 255 a skin remedy is described which, for the purpose of enhancing oxygen transport in the skin, consists of asymmetrical lamellar aggregates built up from phospholipids with a content of phosphatidyl choline ranging from 30 to 99 wt.-% which, unlike the well-known aqueous liposomes, contain perfluorocarbons or mixtures ranging from.1 to 100% w/v in a vehicle suitable for dermatological application. In the known systems, aliphatic, straight-chain and branched perfluoralkanes, mono- or bicyclic, fluoralkyl-substituted perfluorocyclo alkanes, perfluorinated aliphatic or bicyclic amines, bis-(perfluoralkyl)-ethenes or mixtures thereof are described as perfluorocarbons, and of this group perfluorodecalin, perfluoroobutyltetrahydrofuran, perfluorotributylamine, perfluoroctyl bromide, bis-fluoro (butyl)-ethene or $C_6$–$C_9$ perfluoralkanes are preferred. Penetration into the skin is said to be controlled by the carrier structure of the phospholipid aggregates, but especially by the perfluorocarbons according to their critical temperature of solubility in n-hexane, the so-called CST temperature. The lower the CST temperature is, the better is the penetration. The CST temperatures of the perfluorocarbons named preferentially in this claim are all above +22° C.

Accordingly, a skin medication on the basis of semifluorinated diblock or triblock alkanes, especially the fluid, unbranched compounds of the $R_FR_H$ type are proposed, which represent outstanding system solutions. As stated earlier, the semifluorinated alkanes according to the invention are easily to moderately soluble in hydrocarbons and derivatives thereof, the solubility increasing as the $R_H$ content increases and the $R_F$ content decreasing in the semifluorinated alkane. For example, the compounds $C_2F_5$—$C_8H_{17}$ and $C_4F_9$—$C_{10}H_{21}$ dissolve in thin to thick liquid paraffins which find use as pharmaceutical oils and adjuvants (60–230 mPa/s), pump oils or motor oils. As the paraffin oil viscosity increases the solubility decreases, but even in Vaseline, $R_FR_H$'s with a long $R_H$ content are still dissolved. In some cases dissolving can be accelerated or facilitated with the aid of physical emulsifying methods (ultrasound or Gaulin homogenizer or Ultraturrax dispersing machine).

These $R_FR_H$'s are also soluble in silicone oils, as already explained.

Thus, without the aid of emulsifiers or tensides it is possible to prepare a gas-transporting skin remedy or salve, in which the oxygen or carbon dioxide transport is based on their very good solubility in semifluorinated alkane. Also, as already mentioned [R. J. Twieg et al., Macromolecules 18 (1985) 1361], solutions of semifluorinated alkanes of the $R_FR_H$ type can be made in hydrocarbons which pass into a viscous gel state below a characteristic transition temperature. Such gels are formed, for example, of $F(CF_2)_n(CH_2)_mH$ with n=12 and m=8–20 in decane as solvent, or with n=10 and m=12 in octane, decane, dodecane, tetradecane, hexadecane or cyclodecane as solvents. The transition temperatures of homogeneous, fluid solution and viscous gel are given for these systems in FIG. 3; for the claimed application purpose they are within an optimum range of skin and room temperature.

The tissue penetration is due to the lipophilia of the oxygen carrier. Perfluorocarbons are far less lipophilic than the semifluorinated alkanes according to the invention, and their lipophilia is based on the $R_H$ part of the molecule. In harmony with this, the CST temperature in the semifluorinated alkanes of the $R_F R_H$ type is entirely below −22° C., while for most perfluorocarbons it is above +20° C.

Thus, for very quick absorption into the corneal region of the skin and in adjacent tissue, the use of the $R_FR_H$'s claimed according to the invention offers a significant advantage over all of the perfluorocarbon compounds described in U.S. Pat. No. 4,366,169, GB 2087882, EP 29 66 61, DE 41 27 442, and DE 42 21 255.

Saturation with the oxygen of atmospheric air offers a higher oxygen capacity than any of the comparable known systems. The yielding of oxygen to neglected tissue takes place through a topical application.

As described in the beginning, the semifluorinated alkanes according to the invention can be made very easily into stable, aqueous emulsions of the o/w and w/o types with asymmetrical lamellar aggregates, by means of biocompatible emulsifiers (natural phospholipids, such as soya or egg lecithin or synthetically prepared lecithins, or phospholipid mixtures with a content of 60–98% of phosphatidylcholine or ethylene oxide-propylene oxide block polymers, Pluronic®, etc.) with the aid of physical emulsification methods (ultrasound or Gaulin homogenizer, Ultraturrax dispersion machine). Thus the systems thus prepared constitute the effective, gas-transporting substance in salves, cremes, pastes, lotions and other aqueous or alcoholic dermatological formulations as well as in powders. The skin remedy according to the invention can be applied to bandages, plasters, wound coverings and other means coming in contact with the skin.

There is a useful application for oxygen-starved fatty tissue (cellulitis) and for deficiencies due to arteriosclerosis ("smoker's leg," etc.) and for the treatment of burns wherein the damaged tissue remains covered over a long period with the ointment bases according to the invention, and at the same time is supplied with oxygen. By supplying oxygen through the coating, anoxia of the underlying tissue is prevented. Besides, the body's own production of collagen is stimulated, which is an oxygen consuming process due to the oxidation of proline to hydroxyproline. The in vivo production of collagen is directly connected with the healing of skin injuries. The paste bases and salve bases named according to the invention also serve for bedsore prophylaxis and treatment in bedridden patients, e.g., in cases of leg fracture, long-term assisted breathing after poisoning, polytrauma or organic insufficiency.

The salve bases according to the invention furthermore serve for protection against contact dermatitis.

It is known that oxygen-saturated liquid perfluorocarbons, such as perfluordecalin, are used in certain surgical interventions such that this perfluorocarbon is directly fed into the lungs through a tube introduced into the trachea and thus enters the alveolar system. Respiration is then assured through the oxygen-saturated perfluorocarbon and collapse of the lungs is at the same time prevented.

The use of artificial respiration via fluid intubation with the aid of the semifluorinated diblock or triblock alkanes to ease respiration is also possible for the opening of lungs with atelectasis. in lung obstructions for the opening of collapsed lungs, and in the artificial respiration of astronauts, which has not yet been mentioned and is similar to that of divers.

This liquid respiration is possible even in divers with the aid of the semifluorinated alkanes according to the invention. The medium carrying $O_2$ or $CO_2$ put into the lungs through the tube can be constantly enriched with $O_2$ by means of an oxygenator through a circulatory system and freed of $CO_2$ by means of a corresponding $CO_2$ trapping system. A diver thus supplied no longer needs to breathe air or oxygen from compressed-air bottles and exhale through a system of valves. The valve noises and the issuing gas and air bubbles enable the diver to be found by means of sensitive sonar systems.

In the known liquid artificial respiration there are difficulties both in surgical interventions and in the case of divers because, due to the high density of perfluorocarbon (approx. 1.8–2.0 g/cm$^3$) the breathing or transport of the oxygen and carbon dioxide carrying medium is made difficult by a weakened or stressed body.

The advantage of the invention consists in the use of the fluid, liquid semifluorinated alkanes, especially $C_6F_{13}C_8H_{17}$ (b.p. 220° C.), $C_4F_9C_5H_{11}$ (b.p. 131° C.), $C_2F_5C_8H_{17}$ (b.p. 159° C.), $C_2F_5C_4H_8C_2F_5$ (b.p. 138° C.), $C_2F_5C_6H_{12}C_2F_5$ (b.p. 200° C.), $C_3F_7C_2H_4C_3F_7$ (b.p. 115° C.), $C_3F_7C_4H_8C_3F_7$ (b.p. 180° C.). In the case of gas solubility similar to the perfluorocarbons ($R_FR_H$ approx. 45–52 vol. %, $R_FR_HR_F$ approx. 145–150 vol. % $CO_2$), the density of the proposed liquid semifluorinated alkanes amounts to only 1.1–1.5 g/cm$^3$ (25° C.).

The advantages which the use of the proposed semifluorinated alkanes in the described and still scarcely known methods of instillation and fluid artificial respiration offers over the perfluorocarbons, which anyway are no more than conceivable for this purpose, are thus definitely to be found in easier respiration.

It is known to add perfluorocarbons and perfluorocarbon derivates to lubricant oils and waxes as friction reducing agents. It is also known to cover heavily stressed wall materials with thin coatings of fluoropolymers to reduce friction.

In DD 207310 friction reducing additives are described for motor oils, pump oils and silicone oils, consisting of 0.1 to 10 wt.-% of perfluoroalkylethers or -thioethers of the formula R—X—$R_1$ where R=$C_{4-10}$-perfluoralkyl or $C_nF_{2n-1}$, n=8–10), X=S or O, and $R_1$=$C_8H_{17}$, $C_{12-25}$, $CH_2CH_2OH$, or $CH_2CH_2OEt$).

In DD 289424 lubricant additives on the basis of monofluorinated or oligomeric fluorinated hydrocarbons are described, which contain in addition to CF bonds, bonds with weakly bonded moieties such as Cl, OH, OR, SH and SR, R representing an amine and/or $NH_4^+$—, $Ba^{2+}$—, or $Zn^{2+}$— salt of monofluorophosphates or fluorophosphonates. Such a lubricant may also contain a nonionic fluorine tenside, $C_nF_{2n-1}O(CH_2CH_2O)_mH$, where n=8–11 and m=1–4, as emulsifier. The additives are described as usable for metal-to-metal surfaces in machines.

In R. C. Bowers et al, Lubric. Engng. 12 (1956) 245 there is described the use of fluoresters, synthesized from aliphatic dibasic acids and fluorinated alcohols, as additives for heat-resistant oily and waxy lubricants for reducing wear on steel surfaces.

According to V. S. Isakovich et al, Trenie Iznos 13 (1992) 306 the presence of chemosorbed, hydrophobic coatings of fluorine tensides or perfluoresters leads to a reduction of friction of steel against steel.

In W. R. Jones et al., NASA Report TM-87284 (1986) perfluoralkyl ethers of low molecular weight are described as lubricants for extremely low temperatures, in outer space, for example.

In S. Mori, W. Morales, Wear 132 (1989) 111 the tribological reaction of perfluoralkyl polyether oils with steel under high vacuum conditions at room temperature is studied and it is found that, due to tribological reactions, metal fluorides are formed which in turn have a catalytic action on the decomposition of perfluorether. Furthermore, the fluorides formed on the friction path act as boundary layers with simultaneous reduction of the coefficient of friction.

According to K. von Werner, EP 0 545 174 A1 (1993) oligomers of fluorinated olefins of the type $X(CF_2)_{2-16}$—$O_{0\ or\ 1}$—CH=$CH_2$, where X=H or F are described as adjuvants for the application of fluoralkane waxes and as lubricants for the shaping and extrusion of polyethylene.

A series of publications on the application of thin coatings of fluorinated polymers to steel, ceramic or other inorganic materials and the friction-reducing effect on surfaces prepared in this manner are described by way of example in D. L. Cho, H. Yasuda, J. Appl. Polymer Sci.: Appl. Polymer Symp. 42 (1988) 139. The application of plasma-polymer films significantly reduces the friction of sliding parts, e.g., in combustion chambers.

On the other hand, in comparison with the known compounds, the semifluorinated alkanes according to the invention have outstanding properties as friction-reducing additives for highly stressed lubricant oils, waxes, hydraulic fluids and compressor fluids.

As initially described, semifluorinated alkanes are physically, chemically and physiologically inert. Due to the closed hydrocarbon-alkane groups, —$(CH_2)_m$—, —$(CHR_H)_M$—, —$(R_HCR_H)$—, —$(CH_2)_mH$, —$(CHR_H)$, —$(-R_HCR_H)H)$, the CF bonds in the perfluoroalkyl groups directly bonded thereto, —$(CF_2)_n$—, —$(CFR_F)$—, —$(R_FCR_F)$—, —$(CF_2)F$, —$(CFR_F)F$, and —$(R_FCR_F)F$, (in comparison with the CF bonds in the pure perfluorocarbons) are further strengthened. Intramolecular HF cleavage with the formation of fluoroolefinic double bonds does not occur. Thus, for the application according to the invention as friction-reducing additives in greatly stressed oils, corrosion phenomena are also excluded.

The synthesis of this class of compounds on the technical scale is simple (see the Examples of syntheses of semifluorinated diblock and triblock alkanes below). Use as additives in lubricants ranges from 0.1–10 wt.-%, preferably in closed systems. Thus, problems of ecological damage are minor or irrelevant.

The semifluorinated alkanes according to the invention are of an amphiphilic character. Especially compounds of the $F(CF_2)_n(CH_2)_mH$ type are characterized by low boundary surface tensions (50–58 mN/m at 20° C.), and extraordinarily low surface tensions (15–22 mN/m at 20° C.), due to the fact that the oleophobic and lipophobic $R_F$ groups are bound to the one end of the molecule and the oleophilic and lipophilic $R_H$ groups are bound to the other end.

Due to this amphiphilic, boundary surface active behavior in the case of solutions in paraffins or hydrocarbon waxes or also silicone oils, the $R_FR_H$'s at the boundary surfaces of these systems arrange themselves such that their $R_H$ part reaches into the solvent containing hydrocarbons, while the oleophobic $R_F$ part reaches outward. But such an arrangement also exists in the case of the diblock compounds $F(CF_2)_n(CH_2)_m(CF_2)_nF$, since in the longer-chain molecules, due to the steric arrangement of the molecule, the $R_F$ groups of both ends arrange themselves unilaterally against the long-chain alkane bonding link. The result is the reduction of friction on metal surfaces or ceramic surfaces or polymeric carbon fibers or structures, etc. Furthermore, the result is also a barrier effect against the escape of volatile solvent molecules through these boundary layers.

As mentioned in the beginning, solubility in hydrocarbons and their derivatives increases with a high percentage of alkyl groups, and therefore also in silicone oils, in the case of the $R_FR_H$ with increasing $R_H$ content and decreasing $R_F$ content.

For example, the compounds $C_2F_5C_8H_{17}$ (b.p. 160° C.), $C_4F_9C_5H_{11}$ (b.p. 131° C.), $C_6F_{13}C_8H_{17}$ (b.p. 104° C.), $C_{10}F_{21}C_{12}H_{25}$ (b.p. 64° C.) $C_{12}F_{25}C_{20}H_{41}$ (b.p. 98° C.) are easily soluble for the stated use and at the given concentrations (0.1–10 wt.-%).

Thus, in principle, the addition of these friction-reducing additives in gasoline and Diesel engines is possible, assuming that $R_FR_H$'s of corresponding low boiling point are used.

The barrier effect described above, which is due to the orientation of the semifluorinated alkanes in the boundary surface, also reduces the flammability of lubricants and fuels.

The additives according to the invention find use primarily in lubricating oils and waxes for closed systems.

Consequently the use of the additives in motor oils, transmission oils, and hydraulic and compressor oils is possible.

With improved lubrication the working life and intervals of maintenance of equipment, systems and units that have it will be lengthened, and there will be savings of lubricants and fuels.

As lubricants which are effective even at very low temperatures, semifluorinated alkanes of corresponding low boiling point (FIGS. 1 and 2) are used directly, i.e., without additional lubricant, or also as additives.

DETAILED DESCRIPTION OF THE PREFERRED EMBODIMENTS

Figure 1:
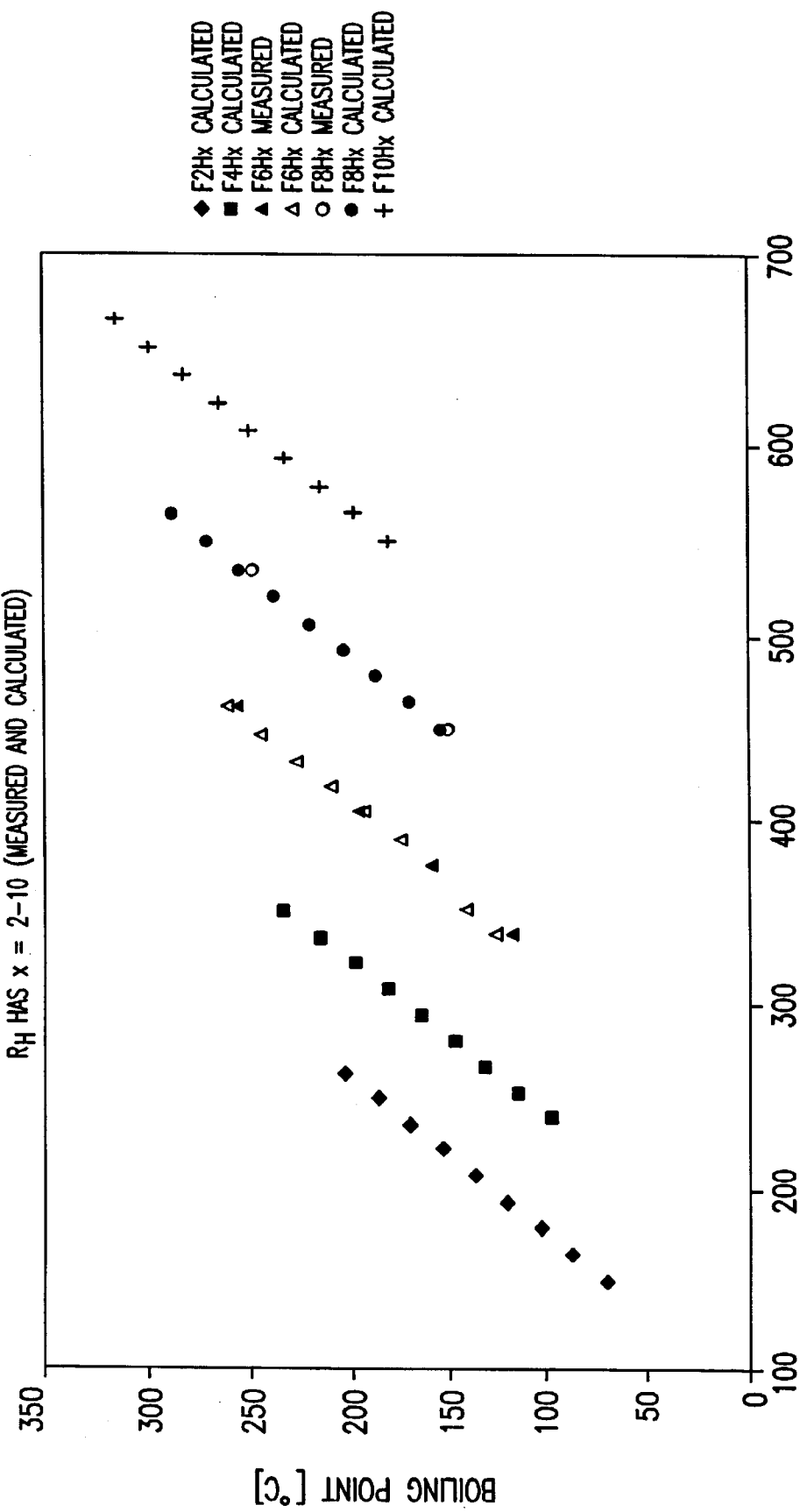
FIG. 1 is a graph showing the boiling points of diblock compounds of the $R_FR_H$ type, wherein $R_H$ has x=2–10 (measured and calculated)
Figure 2:
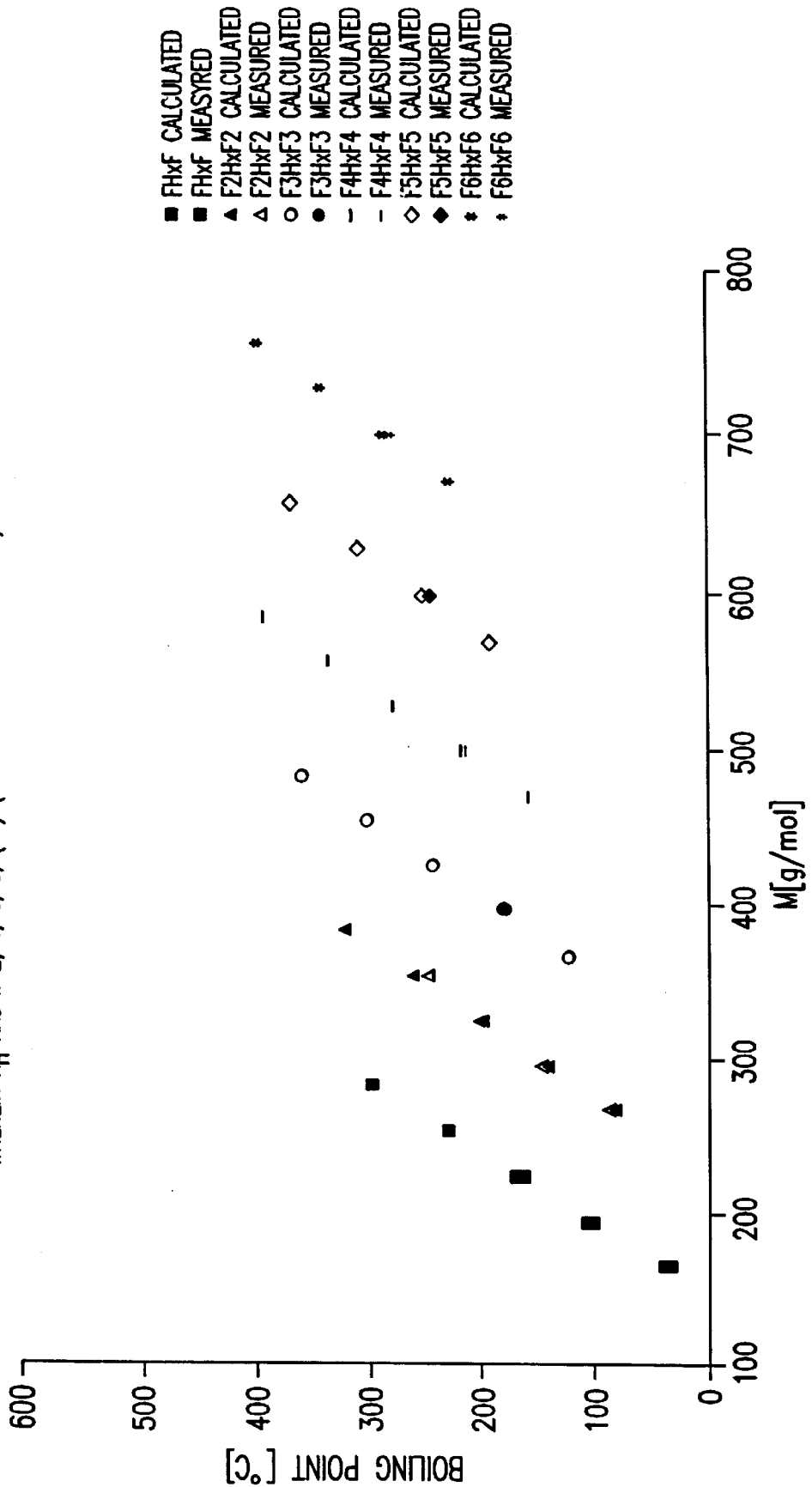
FIG. 2 is a graph showing the boiling points of triblock compounds of the $R_FR_HR_F$ type, wherein $R_H$ has x=2, 4, 6, 8, (10) (measured and calculated)
Figure 3:
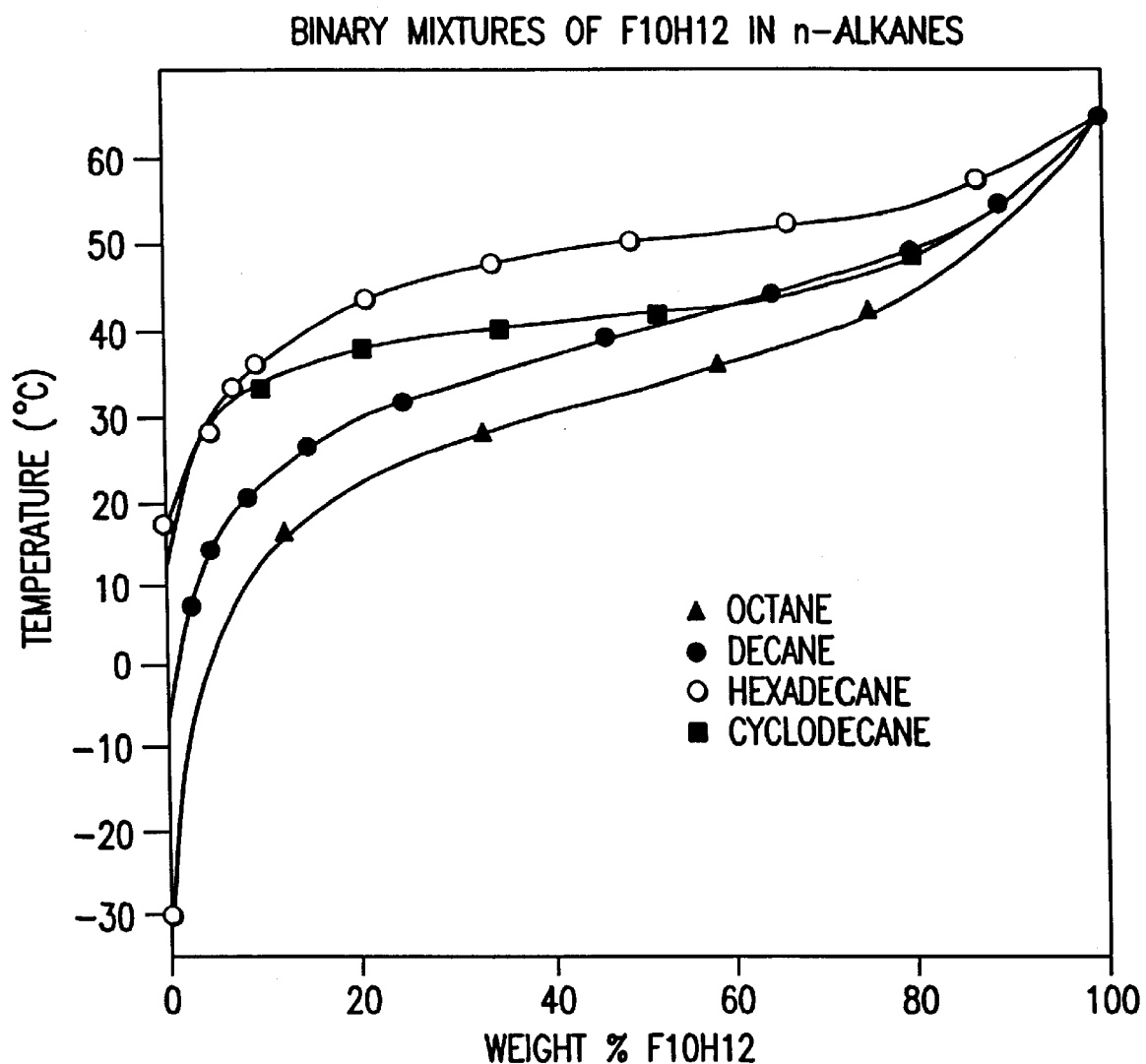
FIG. 3 is phase diagrams of $C_{10}F_{21}C_{12}H_{25}$ (abbreviated: $F_{10}H_{12}$) in octane, decane, hexadecane and cyclodecane according to R. J. Twieg et al., Macromolecules 18 (1985) 1361.

Examples of Syntheses of Semifluorinated Diblock and Triblock Alkanes

EXAMPLE 1

In accordance with K. von Werner, DE 39 25 525 A1 (1989), in a four-necked flask of 250 cm³ capacity, which is equipped with a dropping funnel (with bypass for pressure equalization), vane stirrer, thermometer and reflux condenser with superimposed check valve, 1.82 g (0.075 mol) magnesium chips are placed under argon in 10 cm³ of anhydrous di-n-propyl ether and activated with a few drops of methyl iodide with gentle heating. The temperature is raised to 80° C. while a mixture of 23.7 g (0.05 mol) of $C_6F_{13}CH_2CH_2I$ and 60 cm³ of anhydrous di-n-propyl ether is added drop by drop within one hour with vigorous stirring. Then the mixture is stirred with refluxing for 9 hours and then cooled to 10° C., hydrolyzed with 100 cm³ of 5 wt.-% aqueous hydrochloric acid until the excess magnesium has dissolved. Then the ether phase is separated and concentrated with a rotary evaporator. The oily residue thus obtained is treated with 30 cm³ of chloroform and let stand for 1 hour at 0° C. The solid product precipitated from the mixture is suction filtered and dried in the desiccator. 11.0 g of $C_6F_{13}(CH_2)_4C_6F_{13}$ is obtained as nearly colorless crystals which have a melting point of 48° C. The yield is 63.2% of the theoretical.

By means of nuclear resonance spectral analysis the following values were obtained (in CDC13 solution with tetramethysilane as internal standard):

$^1$H-NMR: 2.11 PPM ($CF_2C\underline{H}_2$), 1.72 PPM ($CH_2\underline{H}_2$)

EXAMPLE 2

The procedure is as given in Example 1, the following substances being used:

1.82 g (0.075 mol) of magnesium chips 28.7 g (0.05 mol) $C_8F_{17}CH_2CH_2I$ 70 cm³ of anhydrous di-n-propyl ether After hydrolysis with dilute hydrochloric acid the mixture is filtered, the raw product is washed with water and dried in the desiccator; then it is recrystallized from chloroform and vacuum dried. 14.9 g of colorless chips are obtained of the compound $C_8F_{17}(CH_2)_4C_8F_{17}$ which have a melting point of 92 to 93° C. The yield is 66.8% of the theoretical.

In the nuclear resonance spectral analysis the following values were obtained:

$^1$H-NMR: 2.12 ppm [$CF_2C\underline{H}_2$, $^3$I(HF)=18.2 Hz], 1.73 ppm ($CH_2C\underline{H}_2$)

$^{13}$C-NMR: 31.17 ppm [$CF_2C\underline{H}_2$, $^2$I(CF)=22.6 Hz] 20.37 ppm ($CH_2C\underline{H}_2$)

EXAMPLE 3

The procedure is as described in Example 2, but after the magnesium chips are activated with methyl iodide, 93.6 mg (0.143 mmol) of the compound $[(C_6H_5)_3P]_2CoCl_2$ is added as catalyst. After recrystallization of the reaction product from chloroform and drying it in vacuo, as described in Example 2, 16.6 g of the compound $C_8F_{17}(CH_2)_4C_8F_{17}$ is obtained, which has a melting point of 92 to 93° C. The amount obtained) corresponds to 74.1% of the theoretical.

Nuclear resonance spectral analysis gives the same values as given in Example 2.

EXAMPLE 4

The operation is performed again as given in Example 2, but after the magnesium chips are activated, 2.2 g [0.005 mol=10 mol-% with respect to the compound of the formula ($C_8F_{17}CH_2CH_2I$) of the compound $C_8F_{17}CH=CH_2$ is added together with the mixture of anhydrous di-n-propyl ether and the compound $C_8F_{17}CH_2CH_2I$. After the reaction product is recrystallized out of chloroform and vacuum-dried, 17.5 g of the compound $C_8F_{17}(CH_2)_4C_8F_{17}$ is obtained, which has a melting point of 92 to 93° C. The amount produced corresponds to 78.1% of the theoretical.

Nuclear resonance spectral analysis gives the same values as given in Example 2.

After filtration of the crude product, the phase containing di-n-propyl ether is separated from the filtrate and dried with sodium sulfate. Gas chromatography of the ether solution thus obtained gives a content of 2.31 g of the compound $C_8F_{17}CH=CH_2$. The 2.2 g of this compound originally put in evidently remains unchanged, so it acts as a catalyst; moreover a small amount of the same compound forms during the reaction with magnesium out of the perfluoroctylethyl iodide.

EXAMPLE 5

Work is performed as described in Example 1, the following substances being used:

1.82 g (0.075 mol) of magnesium chips 30.1 g (0.05 mol) $C_8F_{17}(CH_2)_4I$ 70 cm³ of anhydrous di-n-propyl ether After hydrolysis with dilute hydrochloric acid the mixture is filtered, and the filtered crude product is washed with water and dried in the desiccator. After recrystallization out of chloroform and vacuum drying 14.3 g is obtained of the compound $C_8F_{17}(CH_2)_8C_8F_{17}$ as colorless leaves which have a melting point of 84.5° C. The amount produced corresponds to 60.1% of the theoretical.

In the nuclear resonance spectral analysis the following values are obtained: Classification: $C_8F_{17}$—$CH_2$—$CH_2$—$CH_2$—$CH_2$—$CH_2$—$CH_2$—$CH_2$—$CH_2$—$C_8F_{17}$ $^1$H-NMR: (1)/(8) 2.01 ppm, (2)/(7) 1.62 ppm, (3)/(4)/(5) and (6) 1.38 ppm $^{13}$C-NMR: (1)/(8) 31.21 ppm, [$^2$I(CF)=22.1 Hz], (2)/(7) 20.34 ppm, (3)/(4)/(5) and (6) 29.17 ppm.

EXAMPLE 6

The operation is performed according to K. von Werner, DE 39 25 525 A1 (1989), but instead of the compound $C_8F_{17}CH=CH_2$ after activation of the magnesium chips, 1.2 g [0.0025 mol=5 mol-%, with respect to the amount of compound $C_8F_{17}(CH_2)_4$] of the compound $C_8F_{17}(CH_2)_2CH=CH_2$ is added as catalyst. After work-up 16.2 g of the compound $C_8F_{17}(CH_2)_8C_8F_{17}$ is obtained which has a melting point of 84.5° C. The amount produced corresponds to 68.2% of the theoretical yield.

EXAMPLE 7

Preparation of semifluorinated diblock alkanes according to H. Meinert, A. Knoblich, Biomat. Art. Cells & Immob. Biotech., 21 (1993) 583.

2 mmol of perfluoroalkyl halide and 4 mmol of alkene(1) were dissolved in 15 ml of octane, degassed with argon and heated to 90° C. Then 150 mg of azo-isobutyryl nitrile was added within 30 min, divided among several portions. A slight yellowing of the solution occurred. Then the mixture was distilled. The desired compounds of the type $R_F$—CHI—$CH_2$—$R_F$ were able to be distilled at a reduced pressure of <0.5 mbar. The yield amounted to 85 to 90% with respect to the input amount of perfluoroalkyl halide in the iodides and 22% in the bromides.

Reduction of the Perfluoroalkyl Alkylhalides 6.6 mmol of perfluoroalkyl alkylhalide was dissolved in 15 ml of diethyl ether and 5 ml of acetic acid was added. The mixture was heated to 50° C. and 4 mmol of zinc was added. After cooling, water was added and the phases were separated. The organic phase was dried and distilled. Up to 68% of a mixture of semifluorinated alkanes and alkenes (5.1) and about 10% of dimerization product were isolated.

EXAMPLE 8

Preparation of semifluorinated triblock alkanes according to H. Meinert, A. Knoblich, Biomat. Art. Cells & Immob. Biotech., 21 (1993) 583.

To 30 ml n-dibutyl ether and 4 g of magnesium, 4 g of $C_6F_{13}C_2H_3$ was added, and the temperature raised to 120° C. Then 40 g $C_6F_{13}C_2H_4I$ dissolved in n-dibutyl ether was added. After about 90 minutes the solution had a dark black color, which after a while vanished again. Then the mixture was filtered and water was carefully added; the separated organic phase was dried and distilled. The highest-boiling fractions were placed overnight in the ice box at −20° C. $C_6F_{13}C_4H_8C_6F_{13}$ settled out as a white precipitate. This was filtered out and vacuum dried.

Preparation with Butyl Lithium 3 g of $C_6F_{13}C_2H_4$ and 4 ml of 1.6m of butyl lithium in hexane were added to 5 ml of hexane and heated to 60° C. After about 10 minutes a white precipitate began to settle out. The temperature was maintained for another 50 minutes. Then water was cautiously added and the phases were separated. The organic phase was dried and distilled. The next operation was similar to the reaction with magnesium. The ratio of production of $R_FR_HR_HR_F$ to $R_FR_H$—Bu was determined by gas chromatography. Perfluorodecalin was used as the standard. The total yield was 3.1 g (85%).

The compounds were identified by comparison with the known substances by gas chromatography, MS and $^1$H-NMR.

EXAMPLE 9

As in J. Höpken et al., Macromol. Chem. 189 (1988) 911 the synthesis is performed of $F(CF_2)_{12}(CH_2)_nH$ (n=4, 6, 8, 10, 12, 14, 16, 18, 20), $F(CF_2)_{10}(CH_2)_8(CF_2)_{10}F$ and $F(CF_2)_{12}(CH_2)_{10}(CF_2)_{12}R$ by reacting perfluorodecyl iodide or perfluorododecyl iodide by radical addition with the corresponding alkenes or dialkenes and then reducing the corresponding perfluoroalkyl iodide with tributyltin hydride and AIBN in toluene.

EXAMPLE 10

As in Organikum, Autorenkollektiv, Dtsch. Verlag der Wissenschaften, Berlin (1977) 363, first the perfluoralkyl iodide is formed as in Example 9, but then follows reduction to the semifluorinated alkane, $R_FR_H$ and $R_FR_HR_F$, with palladium charcoal or platinum oxide as catalyst, with hydrogen at 4 bar in the autoclave.

What is claimed is:

1. A method for liquid artificial respiration by intubation, comprising administering at least one semifluorinated alkane of the general formula $R_FR_H$ or $R_FR_HR_F$ wherein $R_F$ is a linear or branched perfluoroalkyl group and $R_H$ is a linear or branched, saturated alkyl group, wherein the linear semifluorinated alkane has the formula:

$F(CF_2)_n(CH_2)_mH$ or $F(CF_2)_n(CH_2)_m(CF_2)_nF$, the branched semifluorinated alkane includes within the perfluoralkyl groups —FCX— units where X=$C_2F_5$, $C_3F_7$ or $C_4F_9$ and within the alkyl groups —HCY— units where Y=$C_2H_5$, $C_3H_7$ or $C_4H_9$, contained within a perfluoralkyl chain is a —$CX_2$— group and contained within an alkyl chain is a —$CY_2$— group, and wherein further the total number of the carbon atoms in the perfluoralkyl part is between 1 and 20, and in the alkyl part the number of the carbon atoms is between 3 and 20.

2. A method according to claim 1, wherein the at least one semifluorinated alkane is at least one of $C_6F_{13}C_8H_{17}$, $C_4F_9C_5H_{11}$, $C_2F_5C_8H_{17}$ or $C_4F_9H_{16}C_4F_9$.

3. A method according to claim 1, wherein the at least one semifluorinated alkane has the general formula $F(CF_2)_n(CH_2)_mH$ or $F(CF_2)_n(CH_2)_m(CF_2)_n$.

* * * * *